(12) United States Patent
Jansky et al.

(10) Patent No.: US 9,574,979 B2
(45) Date of Patent: Feb. 21, 2017

(54) METHOD AND DEVICE FOR TESTING BATTERY PLATE PACKS

(75) Inventors: Franz Albert Jansky, Sebersdorf (AT); Rainer Prokop, Buch bei Hartberg (AT); Christian Arzt, Pöllau (AT)

(73) Assignee: ROSENDAHL NEXTROM GMBH, Pischelsdorf (AT)

( * ) Notice: Subject to any disclaimer, the term of this patent is extended or adjusted under 35 U.S.C. 154(b) by 609 days.

(21) Appl. No.: 13/980,436

(22) PCT Filed: May 24, 2012

(86) PCT No.: PCT/AT2012/000147
§ 371 (c)(1),
(2), (4) Date: Aug. 9, 2013

(87) PCT Pub. No.: WO2012/167289
PCT Pub. Date: Dec. 13, 2012

(65) Prior Publication Data
US 2013/0305835 A1 Nov. 21, 2013

(30) Foreign Application Priority Data

Jun. 9, 2011 (AT) .................................. A 858/2011

(51) Int. Cl.
*G01N 3/08* (2006.01)
*H01M 10/42* (2006.01)
*H01M 10/04* (2006.01)

(52) U.S. Cl.
CPC ........... *G01N 3/08* (2013.01); *H01M 10/4285* (2013.01); *G01N 2203/0019* (2013.01);
(Continued)

(58) Field of Classification Search
CPC ....................................................... G01N 3/08
(Continued)

(56) References Cited

U.S. PATENT DOCUMENTS 3,664,655 A 5/1972 Mccain et al.
4,132,313 A 1/1979 Kolosov
(Continued)

FOREIGN PATENT DOCUMENTS

CN 2853199 Y 1/2007
CN 201220223 Y 4/2009
(Continued)

OTHER PUBLICATIONS

AT Search Report, dated Apr. 20, 2012, from corresponding AT application.
(Continued)

*Primary Examiner* — Lisa Caputo
*Assistant Examiner* — Octavia Hollington
(74) *Attorney, Agent, or Firm* — Young & Thompson

(57) ABSTRACT

In order to test battery plate packs (12, 13), the battery plate packs are transported between conveyor belts (5, 6) while compressed to a specified thickness, and the force required for the compression is detected by measuring cells (14) while the battery plate packs are being transported, which measuring cells are associated with a pressing plate (11) associated with one of the conveyor belts (5). If the force deviates from a specified value, the battery plate pack is evaluated as faulty and is ejected.

25 Claims, 2 Drawing Sheets

(52) U.S. Cl.
CPC . *G01N 2203/0248* (2013.01); *H01M 10/0404* (2013.01); *H01M 10/0459* (2013.01)

(58) Field of Classification Search
USPC .......................................................... 73/818
See application file for complete search history.

(56) References Cited

U.S. PATENT DOCUMENTS

| | | | |
|---|---|---|---|
| 4,778,479 | A | 10/1988 | Romling et al. |
| 5,778,479 | A | 7/1998 | Raia |
| 6,279,224 | B1* | 8/2001 | Wirtz .................... B23P 21/004 29/711 |
| 6,865,818 | B2 | 3/2005 | Petrowich |
| 7,011,202 | B2* | 3/2006 | Farmer ............... B29C 65/7861 198/345.3 |
| 8,035,394 | B2 | 10/2011 | Takeno et al. |
| 8,280,543 | B2* | 10/2012 | Grau ...................... H05K 13/08 700/112 |
| 8,802,260 | B2* | 8/2014 | Nakanishi ........... H01M 2/1077 324/426 |
| 2004/0172842 | A1 | 9/2004 | Petrowich |
| 2008/0311462 | A1 | 12/2008 | Yamauchi et al. |
| 2012/0286739 | A1* | 11/2012 | O'Brien, Jr. ........ H01M 2/1077 320/134 |

FOREIGN PATENT DOCUMENTS

| | | |
|---|---|---|
| CN | 201275715 Y | 7/2009 |
| CN | 201493272 U | 6/2010 |
| DE | 19804650 A1 | 8/1999 |
| EP | 0 029 017 A1 | 5/1981 |
| EP | 0 240 915 A1 | 10/1987 |
| EP | 0 506 645 A1 | 9/1992 |
| GB | 2013964 * | 2/1979 |
| JP | 2009-156866 A | 7/2009 |
| JP | 2010-197054 A | 9/2010 |
| KR | 2008-010375 A | 11/2008 |
| KR | 2010-0110327 A | 10/2010 |
| WO | 84/04000 A1 | 10/1984 |

OTHER PUBLICATIONS

International Search Report, dated Oct. 2, 2012, from corresponding PCT application.
English translation of Chinese Office Action and Search Report, dated Jun. 19, 2014, from corresponding CN application.
English translation of Korean Office Action dated May 9, 2015, from corresponding KR application.
English translation of Korean Office Action dated Mar. 15, 2016, from corresponding KR application.

* cited by examiner

METHOD AND DEVICE FOR TESTING BATTERY PLATE PACKS

BACKGROUND OF THE INVENTION

Field of the Invention

The invention relates to a method and a device for testing battery plate packs with the features of the introductory parts of the independent claims that are directed at the method and the device.

Description of the Related Art

In the production of batteries and accumulators, positive and negative battery plates that are accommodated in pockets of separator material ("jacketed") are inserted into the cells of battery housings.

Here, it is not only important that the pack contains the correct number of battery plates, but also that all battery plates contained in the pack are properly accommodated in pockets of separator material.

This also applies especially to pockets of separators that consist of compressible material, such as, for example, glass fiber fleece (AGM=absorptive glass mat-separators).

Packs of jacketed battery plates are tested by, for example, the force being detected that is necessary to compress the battery plate pack to a predetermined dimension (peck thickness), this dimension corresponding to, for example, the internal dimension of one cell in a battery housing into which the battery plate pack is to be inserted. In the known procedure, the process takes place discontinuously, i.e., each battery plate pack must be inserted separately into the test device and removed again from it.

BRIEF SUMMARY OF THE INVENTION

The object of the invention is to propose a method of the initially named type and also a device that allows faster testing.

This object is achieved according to the invention with a method, and with a device.

Preferred and advantageous configurations of the invention are the subject matter of the dependent claims.

The invention makes it possible to ensure that only those battery plate packs are supplied to the further production of batteries or accumulators whose functionality is ensured by the product-specific compression since the compression of the (AGM) separator is used to produce a perfect fit between the separator and plate. The strength of the necessary compression (compaction) depends on the battery type, but it is generally between 15 to 40% compression. Here, overly strong compression should be avoided since the separator material, especially when it is a glass fiber fleece (AGM), can be destroyed.

In order to test the battery plate packs (AGM elements) under defined conditions, according to the invention a dynamic test method is proposed with which the battery plate packs are compressed to a predefined dimension (preferably the inside dimensions of the cell in the battery housing) and the forces that occur in doing so are (continuously) measured.

The procedure according to the invention makes it possible to check battery plate packs within a cycle time of, for example, only 1.5 seconds. This is achieved by, for example, the battery plate packs that are to be tested being run between two bands and being compressed in doing so, the force acting on the bands being measured.

In one embodiment of the invention, it can be provided that the force is measured at several sites successively in time and then a mean value is computed on which the assessment of the battery plate packs is based.

If the measured value of the force that is necessary to compress the battery plate pack to the predefined dimension is within a defined range, the battery plate pack is assessed as being in order. For deviations of the force up or down that indicate that the battery plate pack is faulty, the battery plate pack is removed and not supplied to the further production of batteries or accumulators. An overly high pressure can be necessary if the battery plate pack contains too many plates and/or there is too much separator material in the pack, for example in the form of an unfilled superfluous pocket. An overly low pressure indicates that in the battery plate pack, a battery plate or a pocket of separator material is missing.

In order to prevent the quality of the battery plate packs from being adversely affected, in one embodiment of the invention it can be provided that there are measures for the two belts of the pressing section to run synchronously.

In another embodiment, it can be provided that the bands in the test station have a width that is at least the same size as the width of the battery plate pack that is to be tested.

In order to achieve conditions that are defined as much as possible when measuring the pressing force and to avoid undue heating of the belts, at least in the area in which the compressed battery plate pack is routed, the band of the upper belt and of the lower belt is routed over, for example, ground metal (steel) plates.

In one embodiment of the invention, it can be provided that the lower feeder band (band), especially the band to which the apparatus for measuring the pressing force (measuring cells) is assigned, is attached essentially rigidly to the machine frame; conversely, the upper band on the machine frame can be adjusted in order to be able to adapt the device to different sizes/thicknesses of battery plate packs. During operation, however, the upper band is also held at a given (preset) distance from the lower band.

In order to avoid damage to the device, it can be provided that the upper band and/or the lower band yields (gives way) when a predetermined force, which occurs while a battery plate pack is being conveyed between the bands, is exceeded. This can be achieved by, for example, corresponding spring loading or an overload safeguard.

In addition, within the scope of the invention, it can be provided that the plate pack be weighed following the measurement of the force necessary for compression, and the weighing can also be carried out in the continuous method.

The weighing station that is optionally provided in one embodiment of the invention is built as a dynamic measurement means. Special attention should be paid here that the preliminary load that is acting on the weighing cell is kept as small as possible. The conveyance of battery plate packs in the weighing station can be implemented via straps or bands that can be directly driven. For example, two opposite weighing cells are used for measuring the weight.

Special attention should be paid that all idle rolls and drives have no imbalance. The frame should be built decoupled from all other system parts and should be provided with vibration-inhibiting feet and supports. The band speed can be made variable.

In the invention, following the test station or the weighing station that is optionally provided, there can be an ejection station that is used to separate faulty battery plate packs.

In one exemplary embodiment of the device according to the invention that is proposed for executing the method according to the invention, the upper conveyor belt is adjusted with reference to the lower conveyor belt such that the distance between the two belts corresponds to the inside dimension of the battery box or a dimension desired by the battery manufacturer. Afterwards, the battery plate pack coming from a jacketing machine during transport through the testing station for monitoring of the element thickness between the conveyor belts (bands) is compressed in a blanket manner (the bands/conveyor belts are wider than the maximum plate width) to the aforementioned dimension (thickness) and the resulting (the necessary) force is recorded (detected). Since the separator can be compressed many times more easily than the jacketed battery plates (lead plates), the compression is produced essentially only by compacting the separator material. The force is measured via measuring cells (single, double or multiple version) that are mounted underneath, especially directly under the pressing plate (they can, however, also be mounted on the upper pressing plate). Using a start signal (for example, photoelectric barrier, sensor, but can also take place in a time-controlled manner), the measurement is started. Afterwards, during the transport of a battery plate pack, a plurality of measured values is recorded, and said values are averaged in an evaluation unit so that a single value is obtained. With a stop signal (for example, photoelectric barrier, sensor, but can also take place in a time-controlled manner), the measurement is ended. The determined measured value (mean value) is compared in a control to a setpoint and evaluated using the preset tolerances. If the battery plate pack is in order, it is delivered to further production; if it should not correspond, it is ejected.

If there is a weighing station, the battery plate pack is assessed only after the evaluation of the weight of the battery plate pack.

The control of the system, the evaluation of the measured values, and the input of tolerances and element details (details of the battery plate packs) preferably take place via a PLC (programmable logic controller) and an HMI (human machine interface) unit.

BRIEF DESCRIPTION OF THE DRAWINGS

Other details and features of the procedure according to the invention and of the device according to the invention will become apparent from the following description of one preferred embodiment based on the drawings.

DETAILED DESCRIPTION OF THE PREFERRED EMBODIMENTS

Figure 1:
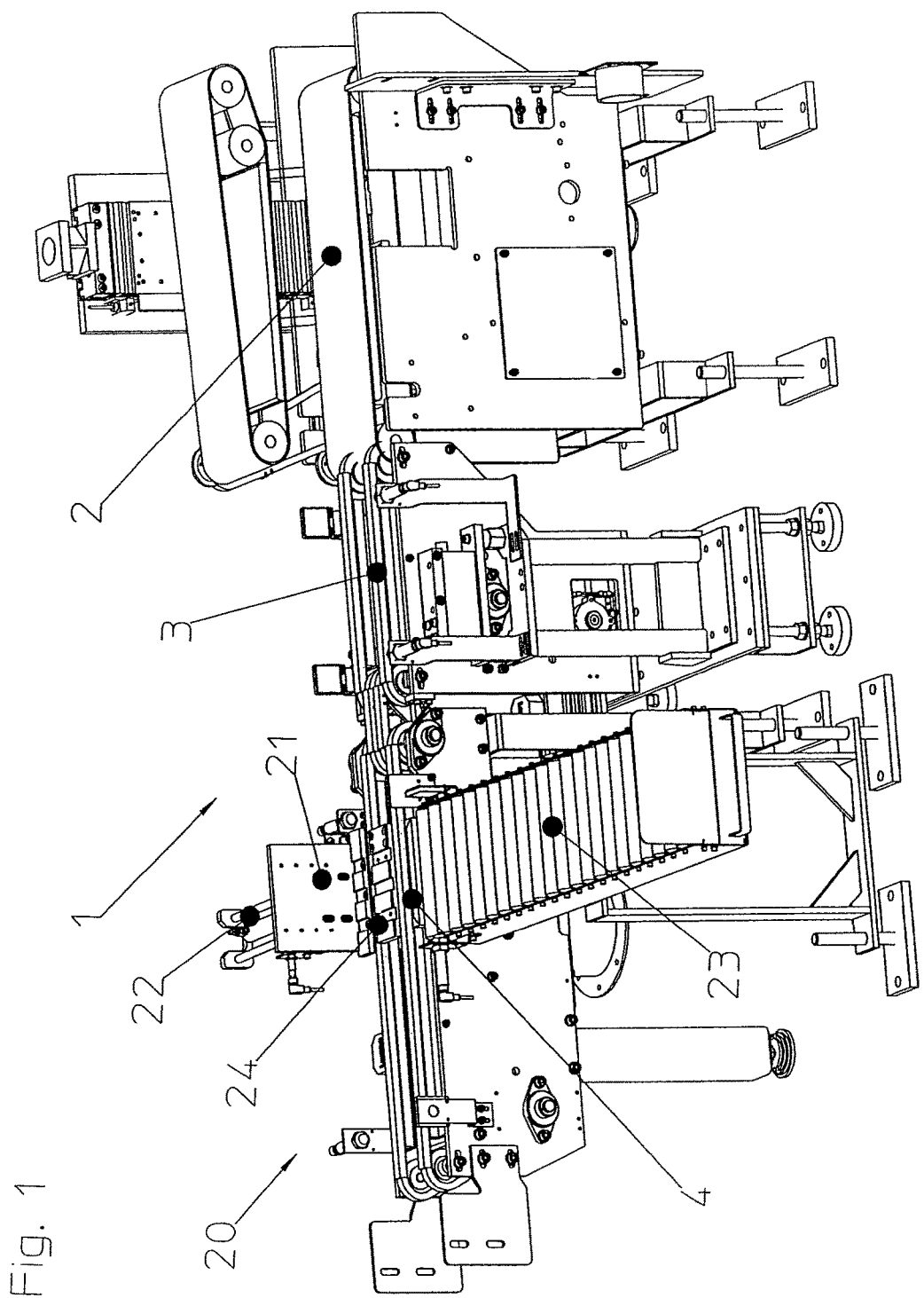
FIG. 1 shows one embodiment of a device according to the invention with a station for element thickness monitoring ("testing station"), a station for the weighing of elements ("weighing station"), and a station for removal, to which an ejection station is assigned.

A device 1 shown in FIG. 1 has a station 2 for testing the thickness of battery plate packs 12, 13 (cf. FIG. 3), a station 3 for the weighing of battery plate packs 12, 13, and an ejection station 4, which is assigned to the removal, designed as a roller conveyor, of the battery plate packs 12, 13.

Figure 2:
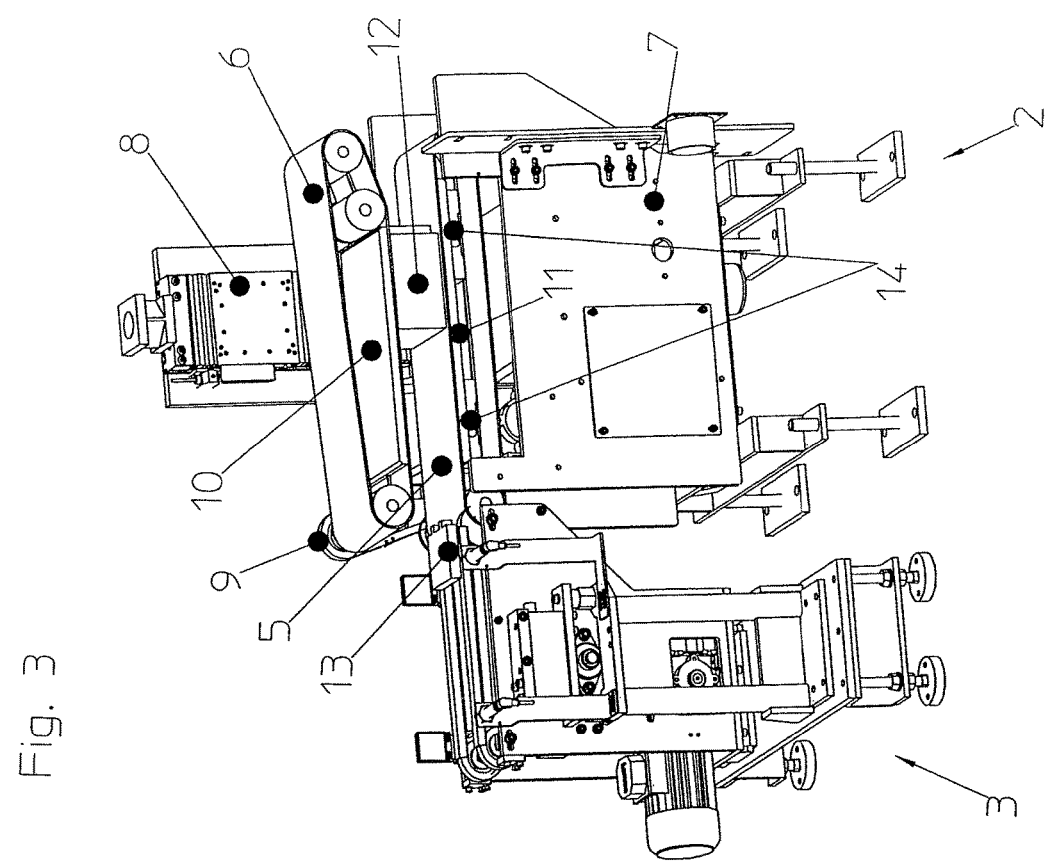
FIG. 2 shows the testing station individually.

In the testing station 2 that is shown in FIG. 2, there are two continuous conveyor belts 5 and 6 (bands) that are moved synchronously by a common drive (toothed belt drive or chain drive 9). In the embodiment of the station 2 that is shown in FIG. 2, the lower conveyor belt 5 is arranged in a stationary manner in the machine frame 7; conversely, the upper conveyor belt 6 can be adjusted using a drive 8 so that the distance between the facing strands of the conveyor belts 5 and 6 can be set in order to allow the testing of battery plate packs 12, 13 of different thickness in the testing station 2.

Figure 3:
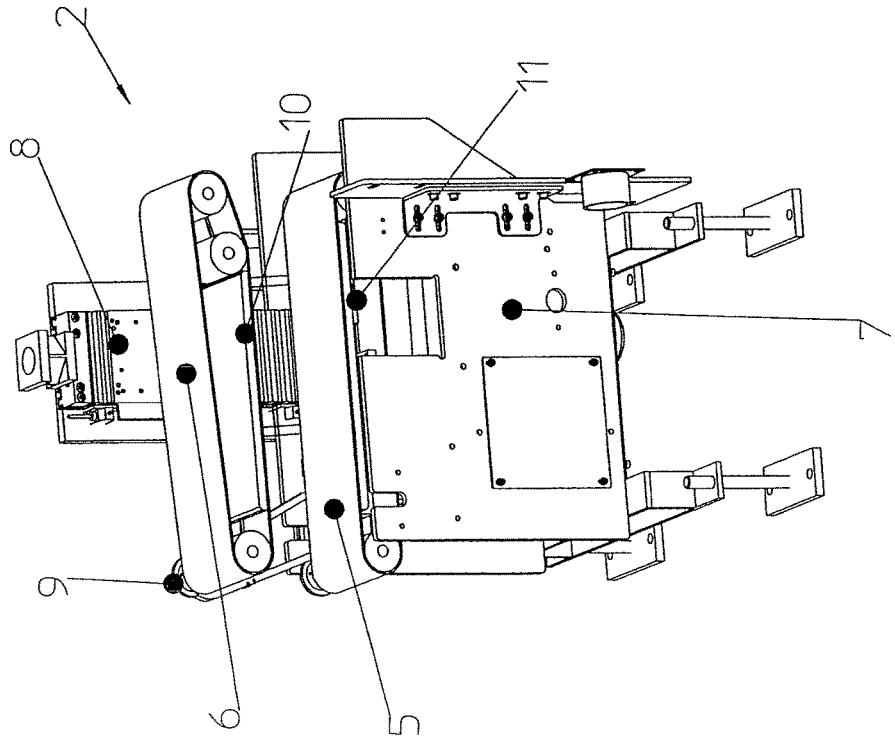
FIG. 3 shows a testing station with a downstream weighing station.

As is shown in FIG. 3, after adjusting the distance between the conveyor belts 5 and 6, thick plate packs 12 as well as thin plate packs 13 can likewise be tested.

The drawings show that the conveyor belts 5 and 6 have a width that is at least as large as the greatest width of battery plates in the battery plate packs 12 and 13.

On the inlet side (on the right in FIGS. 2 and 3), the strand of the upper conveyor belt 6 facing the lower conveyor belt 5 is aligned at an angle so that the battery plate pack 12 or 13 is compressed between the conveyor belts 5, 6 as they arrive.

In the region in which the facing strands of the conveyor belts 5 and 6 are aligned running parallel to one another, there are ground pressing plates 10, 11 (made of steel) that provide for there being defined conditions in this region and for excess heating of the conveyor belts 5 and 6 being avoided.

The lower pressing plate 11, i.e., the pressing plate 11 that is assigned to the lower conveyor belt 5, is assigned measuring cells 14, in the illustrated embodiment there being two measuring cells 14. These measuring cells 14 measure the force that arises when the battery plate pack 12 or 13 passing between the conveyor belts 5 and 6 is compressed to the thickness that is dictated by the position of the upper conveyor belt 6.

As further indicated above, several measurements can be taken that are averaged in order to obtain a mean value that underlies the assessment of the battery plate pack 12 or 13.

On the outlet side (on the left in FIG. 2), a weighing station 3, in which the weight of battery plate packs 12, 13 is determined, is located downstream from the station 2.

Following the weighing station 3, there is a removal 20 for battery plate packs 12 or 13, battery plate packs 12 or 13 that have passed the test and that therefore have the correct number of battery plates and the correct number of pockets of separators being further conveyed.

Battery plate packs 12, 13, which have been assessed as faulty based on the measurement of the pressing force in the station 2 and/or an incorrect weight in the station 3, are ejected in an ejection station 4. This ejection station 4 has a lifting platform 24 that raises the plate packs off the conveyor belt and a plate 21 that can be driven transversely to the conveyor direction using a hydraulic cylinder 22 and that pushes out faulty plate packs laterally onto a roller conveyor 23.

In summary, one embodiment of the invention can be described as follows:

For testing of battery plate packs 12, 13, the latter are transported compressed between feeder bands 5, 6 to a given thickness, and during transport of the battery plate packs 12, 13, the force that is necessary for compression is detected by measuring cells 14 that are assigned to a pressing plate 11 that is assigned to one of the conveyor belts 5. If this force deviates from a given value, the battery plate pack is assessed as faulty and ejected.

The invention claimed is:

1. A method for the testing of at least one battery plate pack, consisting of several positive and negative battery plates that are accommodated in separator pockets, the method comprising:

measuring the force that is necessary to compress the battery plate pack to a given thickness, the compression and the measurement of the force necessary to compress the battery plate pack to the given thickness occurring while the battery plate pack is moving, wherein the force that is necessary for the compression of the battery plate pack is compared to one or more given values, and for a deviation from the one or more values that exceeds a certain tolerance, the battery plate pack is removed.

2. The method according to claim 1, wherein the battery plate pack is moved between two synchronously moving feeder bands.

3. The method according to claim 2, wherein continuous feeder bands are used as feeder bands.

4. The method according to claim 2, wherein the battery plate pack is compressed to the given dimension in the entry region of the feeder bands, and subsequently, the force that is necessary for the compression is measured at at least one site.

5. The method according to claim 2, wherein feeder bands are used that are made continuous transversely to the direction of motion.

6. The method according to claim 1, wherein the force that is necessary for the compression of the battery plate pack to the given thickness is measured at several sites during the movement of the battery plate pack.

7. The method according to claim 6, wherein a mean value is computed from several measured values for the force.

8. The method according to claim 1, wherein following the determination of the force that is necessary for the compression of the battery plate pack to a given dimension, the weight of the battery plate pack is acquired.

9. The method according to claim 8, wherein the weight of the battery plate pack is acquired while the battery plate pack is moving.

10. The method according to claim 1, wherein the weight of the battery plate pack is compared to the one or more given values, and for a deviation from the one or more values that exceeds a certain tolerance, the battery plate pack is removed.

11. A device for the testing of battery plate packs with the method according to claim 1, the device comprising:
a station that is provided for measuring the force that is necessary for compression of the battery plate pack to the given thickness.

12. The device according to claim 11, wherein the station has continuous feeder bands that move parallel to one another in the measurement region.

13. The device according to claim 12, wherein pressing plates that are provided on the side of strands facing the opposite feeder band are assigned to the strands of the feeder bands, the strands being aligned parallel to one another.

14. The device according to claim 13, wherein the pressing plates are metal (steel) plates or plastic plates.

15. The device according to claim 14, wherein the sides of the metal plates facing the strands of the feeder bands are ground.

16. The device according to claim 12, wherein on the inlet side, at least one feeder band has an obliquely aligned region, so that there is a tapering inlet region between the feeder bands.

17. The device according to claim 12, wherein at least one of the feeder bands is disposed adjustably in a machine frame.

18. The device according to claim 12, wherein at least one of the feeder bands is assigned an overload safeguard that releases the feeder band as soon as the force acting on the feeder band exceeds a given value.

19. The device according to claim 11, wherein at least one measuring cell for recording force is assigned to at least one feeder band.

20. The device according to claim 19, wherein several measuring cells are provided.

21. The device according to claim 19, wherein the measuring cell is connected to the plate that is assigned to the feeder band.

22. The device according to claim 11, further comprising a weighing station that is following the testing station for measuring the force that is necessary for compression.

23. The device according to claim 22, wherein the weighing station has continuous feeder bands.

24. The device according to claim 11, further comprising a removal for battery plate packs following the station for measuring the force and optionally the weighing station, and
an ejection apparatus for faulty plate packs coordinated to the removal.

25. The device according to claim 24, wherein the ejection apparatus has a slide that can be adjusted transversely to the conveyor direction of the removal, with a lifting platform, to which a roller conveyor is assigned.

\* \* \* \* \*